United States Patent [19]
Rosborough

[11] Patent Number: 5,620,451
[45] Date of Patent: Apr. 15, 1997

[54] LEAD EXTRACTION SYSTEM FOR TRANSVENOUS DEFIBRILLATION LEADS AND FOR ENDOCARDIAL PACING LEADS

[75] Inventor: John P. Rosborough, Houston, Tex.

[73] Assignee: Intermedics, Inc., Angleton, Tex.

[21] Appl. No.: 428,450

[22] Filed: Apr. 25, 1995

[51] Int. Cl.[6] ................................................. A61B 17/00
[52] U.S. Cl. ................................................ 606/108; 607/126
[58] Field of Search .................... 606/106, 108; 128/657, 642; 607/126, 127, 128, 115, 116

[56] References Cited

U.S. PATENT DOCUMENTS

| | | | |
|---|---|---|---|
| 1,260,924 | 3/1918 | Lossing | 606/106 |
| 4,000,745 | 1/1977 | Goldberg | 128/418 |
| 4,574,800 | 3/1986 | Peers-Trevarton | 128/303 R |
| 4,590,337 | 5/1986 | Engelmore | 179/186 |
| 4,705,823 | 11/1987 | Choi et al. | 524/474 |
| 4,706,671 | 11/1987 | Weinrib | 128/348.1 |
| 4,820,298 | 4/1989 | Leveen et al. | 623/1 |
| 4,848,342 | 7/1989 | Kaltenbach | 128/341 |
| 4,943,289 | 7/1990 | Goode et al. | 606/1 |
| 4,967,766 | 11/1990 | Bradshaw | 128/785 |
| 4,988,347 | 1/1991 | Goode et al. | 606/1 |
| 5,011,482 | 4/1991 | Goode et al. | 606/1 |
| 5,013,310 | 5/1991 | Goode et al. | 606/1 |
| 5,108,417 | 4/1992 | Sawyer | 606/198 |
| 5,133,364 | 7/1992 | Palermo et al. | 128/657 |
| 5,207,683 | 5/1993 | Goode et al. | 606/108 |
| 5,209,735 | 5/1993 | Lazarus | 128/657 |
| 5,269,791 | 12/1993 | Mayzels et al. | 606/1 |
| 5,282,796 | 2/1994 | Knoepfler | 606/1 |

FOREIGN PATENT DOCUMENTS 9306792   4/1993   WIPO ................................ A61F 2/06

OTHER PUBLICATIONS

Cook Pacemaker Corp., "The Cook Pacemaker Lead Extraction System", FM-923B Jul. 1993, Leechburg, PA.
Kenneth A. Ellenbogen, ED., "Cardiac Pacing" Blackwell Scientific Publications, Cambridge, Mass., 1992, pp. 252-256.

*Primary Examiner*—William E. Kamm
*Assistant Examiner*—Kennedy J. Schaetzle
*Attorney, Agent, or Firm*—John R. Merkling

[57] ABSTRACT

A system for lead removal of both heart pacemaker leads and cardioverter-defibrillator endocardial leads comprising a flexible coil of flattened ribbon. Preferably, the ribbon is comprised of polyethylene or another suitable biologically compatible material. At a distal end of the coil, a cutting surface may be provided, such as a chisel-like edge at the distal end of the coil. A handle may be provided for twisting the coil onto the lead. The coil should be at least partially radiopaque or provided with a surface which is radiopaque so that its use may be observed in the body by fluoroscopy or other suitable means.

27 Claims, 2 Drawing Sheets

LEAD EXTRACTION SYSTEM FOR TRANSVENOUS DEFIBRILLATION LEADS AND FOR ENDOCARDIAL PACING LEADS

BACKGROUND OF MY INVENTION

My invention relates generally to cardiac stimulation, and more particularly to a system for removing an implanted endocardial pacemaker lead or an implanted transvenous defibrillation lead from the heart.

Various factors affect the human heart rate and contribute to changes of rate from what is termed the normal sinus rate range (rates generally ranging in adults from 60 to 100 beats per minute). In healthy persons, tachycardia (100 to 160 beats per minute) is experienced as a result of such things as physical or emotional stress (exercise or excitement), consumption of alcoholic or caffeinated beverages, cigarette smoking, or ingestion of certain drugs. Variation from normal sinus rate range is generally characterized as cardiac arrhythmia, and arrhythmia rates exceeding the upper end of the sinus rate range are termed tachyarrhythmias. Arrhythmia rates below the normal sinus rate range are termed bradycardia.

Arrhythmias typically arise in the atria or ventricles as a consequence of an impairment of the heart's electrical electro-physiologic properties such as excitability, conductivity, and automaticity (rhythmicity). Such arrhythmias require special treatment. Cardiac pacemakers, chronically implanted within the patient's body, and connected to the heart by one or more leads, are frequently used to control bradycardia conditions. Implantable cardioverter-defibrillators, also implanted chronically in the patient's body and connected to the heart by one or more leads, can be used to control tachyarrhythmias, life-threatening or not, and life-threatening fibrillations.

There are generally two types of body implantable leads used with cardiac pacemakers—one which requires surgery to expose the myocardial tissue whereby an electrode is affixed to the epicardial tissue and another which can be inserted through a body vessel, such as a vein, into the heart where an electrode contacts the endocardiac tissue. In the latter type, the endocardial lead is often secured to the heart through the endothelial lining by a helix affixed to a distal end of the lead. When the end of the lead contacts the lining of the heart at a desired location, the lead may be secured in place by rotating the lead, thus screwing the helix into the heart tissue. Other types of active or passive fixation have also been used to secure the lead to the inner wall of the heart, such as hooks or tines.

Similarly, cardioverter defibrillators have used both epicardial leads, that is, leads with electrodes attached to the outside of the heart, and endocardial leads, that is, leads inserted into the heart through a body vessel. One such endocardial lead, is described in U.S. Pat. No. 4,922,927 to Fine, et al., assigned to the assignee of my invention.

With either pacing or defibrillation endocardial leads, fibrotic tissue may eventually encapsulate the lead, especially in areas where there is low velocity blood flow. When small diameter veins through which the lead passes become occluded with fibrotic tissue, separating the lead from the vein is difficult and can cause severe damage to or destruction of the vein. Furthermore, separation may not be possible without constricting or containing the movement of the lead.

In most cases, an endocardial lead will outlast its associated implanted device. However, the lead may become inoperative or another type of lead may be required. Frequently, the existing lead is left in place and an additional lead is implanted, rather than risk removal of the old lead, now bonded to the surrounding tissue. Leaving the implanted lead in place, however, particularly in the heart, may further restrict the operation of various heart valves through which the lead passes. If several leads are left in place, the operation of the heart and its efficiency may be impaired.

In addition, infection may occasionally develop in or around a lead, requiring surgical removal. In some cases, surgical removal may involve open heart surgery with its accompanying complications, risks, and costs. These risks are significant for the endocardial pacemaker lead. Because the endocardial defibrillation lead is larger and more complex, the complications associated with the removal of a defibrillation lead can be even greater.

Several methods for removal of pacemaker leads have heretofore been proposed. One method involves a lead removal tool that utilizes a hollow, rigid tube and a beveled rod tip for engaging and deforming the coil structure of the heart lead. However, if such a lead could not be removed because of some complication, the tip of the tool was nevertheless locked in place and could not be removed from the lead. Consequently, both the tool and the lead would have to be surgically removed. Moreover, the rigid tube of the tool could easily puncture a blood vessel or a heart cavity wall.

Another method for transvenously extracting a lead involved manual manipulation without the add of a tool. Such a method is not possible if the lead has become encapsulated in a blood vessel. Moreover, the method puts excessive strain and tension on the polyurethane or silicone insulation surrounding most pacemaker leads. Should the lead break, the broken inner coil and insulation could damage the heart or surrounding blood vessels. Surgical removal of the broken lead would be imperative. Moreover, if the pacemaker lead included times, a cork screw, or other fixation device at the tip, pulling on the lead could seriously damage the wall of the heart.

Another technique has been proposed by Cook Pacemaker Corporation, and is described in a series of U.S. Patents to Goode, et al., beginning with U.S. Pat. No. 4,943,289. This method generally includes the use of a stiffening stylet which can be inserted into the lead and which engages the inner coil of the lead near the tip, allowing tension to be applied through the stiffening stylet close to the tip of the lead. The technique also uses a pair telescopic flexible tubes which are slid over the lead to free fibrotic connections until the tubes are close to the distal tip of the lead.

SUMMARY OF MY INVENTION

My invention provides a system for lead removal of both heart pacemaker leads and cardioverter-defibrillator endocardial leads.

The system comprises a flexible coil of flattened ribbon. Preferably, the ribbon is comprised of polyethylene or another suitable biologically compatible material. At a distal end of the coil, a cutting surface may be provided. My preferred embodiment includes a chisel-like edge at the distal end of the coil. A handle may be provided for twisting the coil onto the lead. The coil should be at least partially radiopaque or provided with a surface which is radiopaque so that its use may be observed in the body by fluoroscopy or other suitable means.

It is a principle object of my invention to provide a lead extraction system which can be used with both cardiac pacemaker and cardioverter-defibrillator leads.

Another object of my invention is to provide a more flexible lead extraction system.

Another object of my invention is to provide a system which can accommodate partially broken leads.

It is also an object of my invention to provide a system which will release an implanted lead from fibrotic attachment to surrounding tissue by rotary action of the system.

Another object of my invention is to provide a cardiac lead extraction system which will support the cardiac lead for extraction.

Another object of my invention is to provide a cardiac lead extraction system which can transmit torque along a cardiac lead, to aid in the withdraw of active fixation mechanisms.

A further object of my invention is to provide a cardiac extraction system which, when not subject to torque, provides a supporting structure through which a cardiac lead may be withdrawn.

These and other objects and features of my invention will be apparent from the following detailed description, taken with reference to the accompanying drawings.

DETAILED DESCRIPTION OF MY PREFERRED EMBODIMENT

Figure 1:
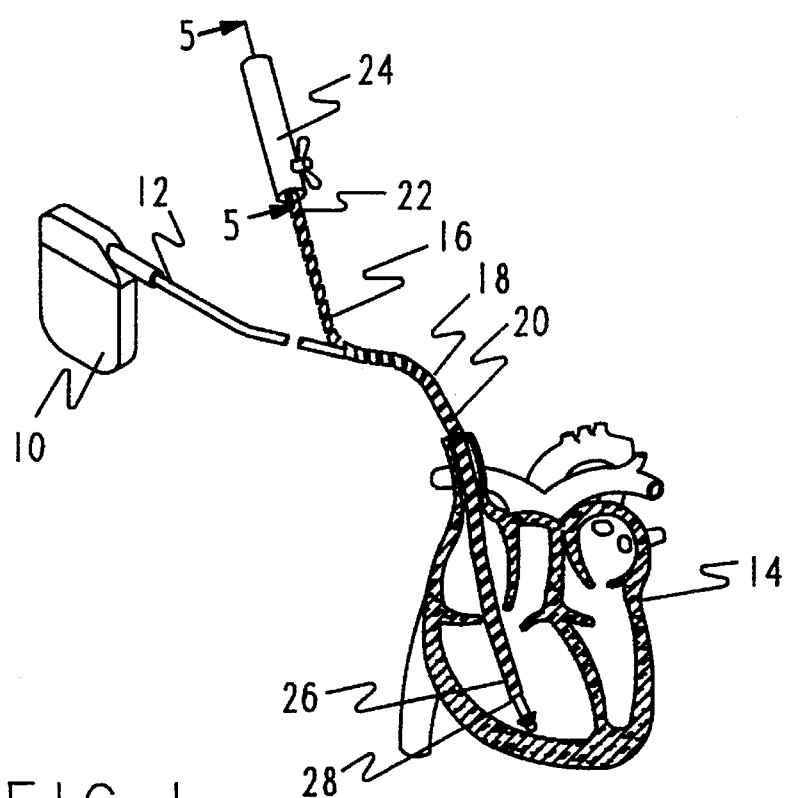
FIG. 1 is a perspective view of an implanted cardiac stimulator with an endocardial lead attached connecting the stimulator to a heart and an extraction system according to my invention.

Referring now to the drawings, in FIG. 1 an implantable cardiac stimulation device 10 is illustrated with an endocardial lead 12 connecting the device 10 to a human heart 14. The stimulation device 10 may be a pacemaker, a cardioverter-defibrillator, or similar device. The endocardial lead 12 may be any elongated lead structure, for example, a pacemaker lead or an endocardial defibrillation lead and electrode. A lead extraction system 16 is illustrated in connection with the endocardial lead 12. The lead extraction system 16 comprises a coil 18 formed of a ribbon 20 of incompressible but flexible material, such as preferably polyethylene or other suitable bio-compatible polymer. A metallic ribbon could also be employed. At a proximal end 22 of the coil 18, a handle 24 may be provided to aid in manipulating the coil.

Figure 3:
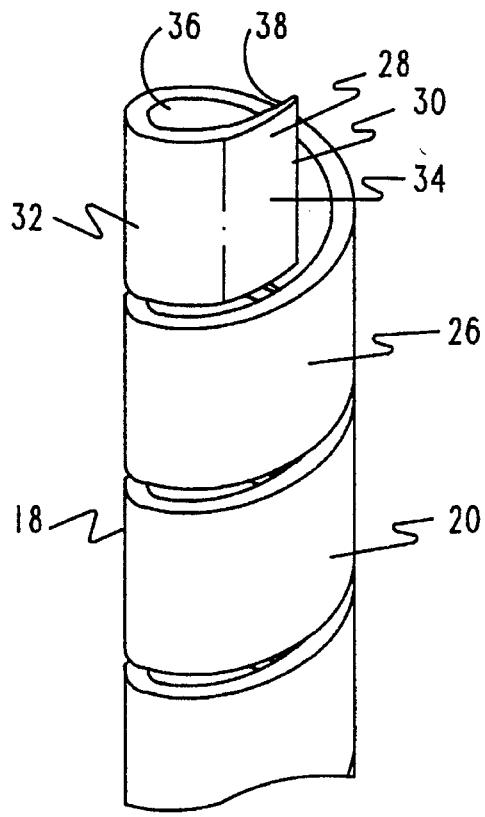
FIG. 3 is a first embodiment of a distal end of the extraction system of FIG. 2.
Figure 4:
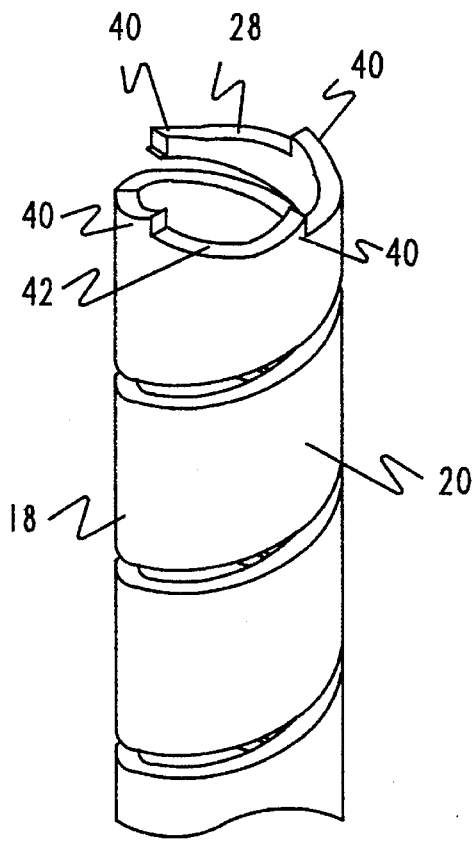
FIG. 4 is a perspective view of a second embodiment of the distal end of the extraction system FIG. 2.

At a distal end 26 of the coil 18, a cutting surface 28 may be provided. Two forms of cutting surface 28 are illustrated in FIGS. 3 and 4. In FIG. 3, my preferred embodiment, the cutting surface 28 comprises a chisel edge 30 substantially parallel to a longitudinal axis of the coil 18. On an outer surface 32 of the coil 18 at the chisel edge 30, there is a taper 34 which reduces the thickness of the ribbon to form the cutting edge. On an inner surface 36 of the coil 18, adjacent the cutting edge 30 there is a short taper 38. Most of the cutting or severing of fibrous ingrowth around the lead 12 is accomplished by the longer outside taper 34. This tends to urge the coil towards the lead as it is twisted around the lead. However, the short taper 38 raises the cutting edge 30 slightly away from the adjacent lead and prevents a cutting edge 30 from cutting into the lead.

Figure 2:
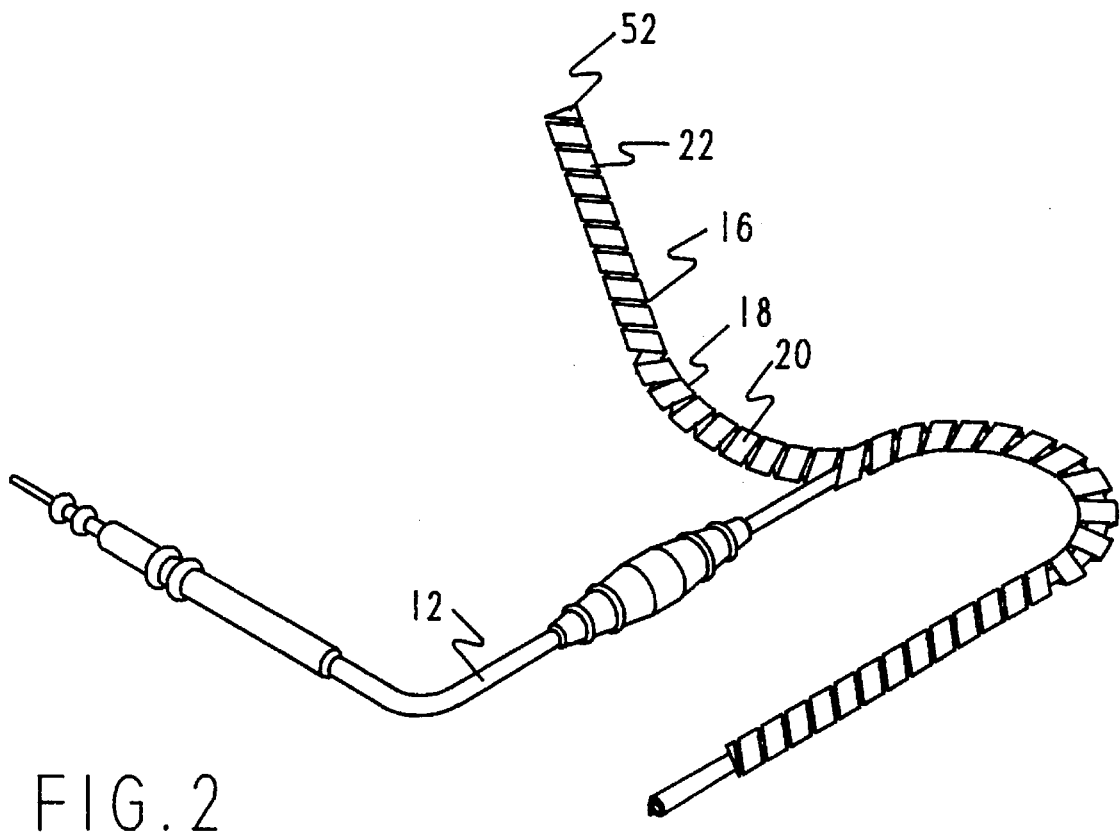
FIG. 2 is a perspective view of an endocardial lead with an extractor system according to my invention.

An alternative embodiment of the cutting edge 28 is illustrated in FIG. 4. In FIG. 4, the coil 20 is truncated perpendicular to its longitudinal axis and a plurality of teeth 40 are provided on a distal edge 42. A plain distal edge, as illustrated in FIG. 2, might also be used. Other forms of cutting edge or an abrasive surface, could also be selected by one skilled in the art.

To use the lead extraction system of my invention, a physician would expose the cardiac stimulation device 10 and connected lead 12. In general, the cardiac stimulation device 10 would then be removed from the lead. The coil 20 of the lead extraction system 18 would be wrapped around the lead 12 by twisting the coil 20 around the lead with a portion of the lead protruding between turns of the coil 20 as illustrated in FIG. 2. By turning the coil, the coil can be carefully advanced along the lead 12 toward the distal end thereof. As the coil is advanced, it will sever fibrous ingrowth. Moreover, because of its turning action, it will pass more readily over broken or ruptured portions of the lead and will also pass over endocardial defibrillation electrodes, which are generally larger and more bulky than pacemaker electrodes. An example of such a defibrillation electrode is disclosed in U.S. Pat. No. 4,922,927. The coiled structure of the extraction system 18 tends to allow the system to follow the curves of the implanted lead and the blood vessels in which the lead is implanted. This makes injury to the surrounding walls of blood vessels less likely.

Figure 5:
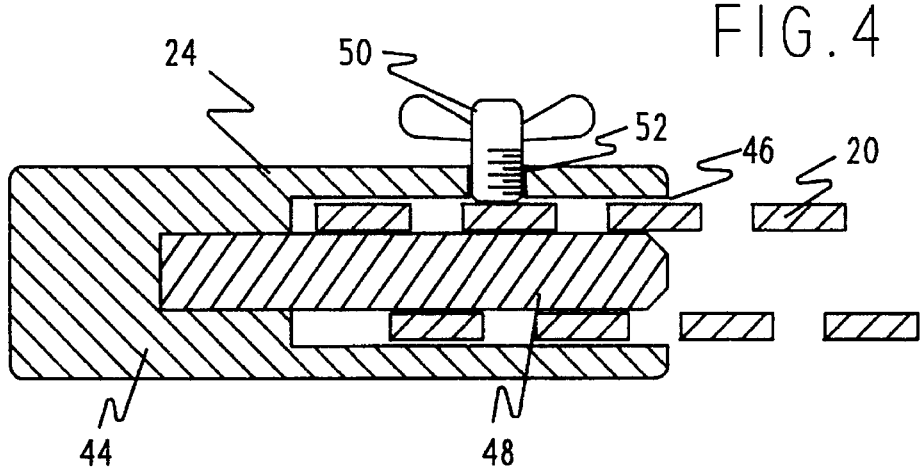
FIG. 5 is a through section of a handle for use with the extraction system taken along line 5—5 of FIG. 2.

The handle 24 may also be used to aid in manipulating the coil 20. A form of a suitable handle 24 is illustrated in section in FIG. 5. The handle 24 comprises a grip 44 with a longitudinal distal stopped bore 46 for receiving the coil 20. A central post 48 fills the central lumen of the coil 20 to give better support to the coil 20. A screw 50 is threadedly received in the bore 52 in the handle. The wing swing 50 tightens against the coil 20 to fasten the handle 24 to the coil.

At the proximal end 22 of the coil 20, a blunt end 52 is provided which can also be used within the body. After the length of the lead has been freed, the system 18 can then be removed from the lead. The handle 24 can then be removed from the proximal end 22 and placed on the distal end 26. The coil 20 is advanced around the lead until the blunt end 52 is adjacent the tip of the lead. Counter-rotating the coil will then release the lead and tend to expand the coil outwardly against the surrounding blood vessels. The lead can then be pulled out through the coil. The blunt end 52 of the coil can provide broader support to heart tissues surrounding the lead tip, allowing the lead tip to be freed from the tissue with less damage to the tissues.

Although my preferred embodiment has been described herein, it will be apparent to those of ordinary skill in the art that variations and modifications of the disclosed embodiments may be implemented without departing from the concepts, spirit and scope of my invention. Accordingly, it is intended that my invention be limited only as required by the appended claims and applicable rules of law.

I claim as my invention:

1. A lead extraction system comprising a coiled, flexible ribbon having a distal end and a proximal end, said flexible ribbon forming a tube adapted to fit over an implanted lead, successive turns of said ribbon lying adjacent one another and spaced apart from one another such that said lead can be passed between two successive turns of said ribbon from an outside of said tube to an inside thereof, and means attached to said distal end of said ribbon for severing fibrous ingrowth surrounding said lead.

2. The lead extraction system according to claim 1 further comprising a handle at said proximal end.

3. The lead extraction system according to claim 2 further comprising means for selectively attaching said handle at said proximal end.

4. The lead extraction system according to claim 3 wherein said means for severing comprise a chisel edge at a distal end of said ribbon.

5. The lead extraction system according to claim 4 wherein said chisel edge has a relatively long bevel on an outward side of said ribbon and a relatively short bevel on an inward side of said ribbon.

6. The lead extraction system according to claim 5 wherein said ribbon is comprised of a bio-compatible polymer.

7. The lead extraction system according to claim 6 wherein at least a part of said ribbon is radiopaque.

8. The lead extraction system according to claim 5 wherein said ribbon is comprised of a bio-compatible metal.

9. The lead extraction system according to claim 8 wherein at least a part of said ribbon is radiopaque.

10. The lead extraction system according to claim 1 wherein said means for severing comprise an abrasive edge at a distal end of said ribbon.

11. The lead extraction system according to claim 10 wherein said abrasive edge comprises a distal edge having a plurality of circumferentially spaced teeth.

12. The lead extraction system according to claim 11 wherein said ribbon is comprised of a bio-compatible polymer.

13. The lead extraction system according to claim 12 wherein at least a part of said ribbon is radiopaque.

14. The lead extraction system according to claim 11 wherein said ribbon is comprised of a bio-compatible metal.

15. The lead extraction system according to claim 14 wherein at least a part of said ribbon is radiopaque.

16. The lead extraction system according to claim 1 wherein said means for severing comprise a chisel edge at a distal end of said ribbon.

17. The lead extraction system according to claim 16 wherein said chisel edge has a relatively long bevel on an outward side of said ribbon and a relatively short bevel on an inward side of said ribbon.

18. The lead extraction system according to claim 17 wherein said ribbon is comprised of a bio-compatible polymer.

19. The lead extraction system according to claim 18 wherein at least a part of said ribbon is radiopaque.

20. The lead extraction system according to claim 16 wherein said ribbon is comprised of a bio-compatible metal.

21. The lead extraction system according to claim 20 wherein at least a part of said ribbon is radiopaque.

22. The lead extraction system according to claim 1 further comprising a blunt end at said proximal end.

23. The lead extraction system according to claim 22 further comprising a handle adapted to be selectively attached at either said proximal or said distal end, whereby either said means for severing or said blunt end can be selectively advanced into the body of a patient.

24. The lead extraction system according to claim 1 wherein said ribbon is comprised of a bio-compatible polymer.

25. The lead extraction system according to claim 24 wherein at least a part of said ribbon is radiopaque.

26. The lead extraction system according to claim 1 wherein said ribbon is comprised of a bio-compatible metal.

27. The lead extraction system according to claim 26 wherein at least a part of said ribbon is radiopaque.

* * * * *